(12) United States Patent
Hill et al.

(10) Patent No.: US 8,896,832 B2
(45) Date of Patent: Nov. 25, 2014

(54) DISCRETE POLARIZATION SCATTEROMETRY

(75) Inventors: Andrew V. Hill, San Jose, CA (US); Amnon Manassen, Haifa (IL); Daniel Kandel, Aseret (IL); Vladimir Levinski, Nazareth Ilit (IL); Joel Seligson, Misgav (IL); Alexander Svizher, Haifa (IL); David Y. Wang, Santa Clara, CA (US); Lawrence D. Rotter, Pleasanton, CA (US); Johannes D. de Veer, Menlo Park, CA (US)

(73) Assignee: KLA-Tencor Corp., Milpitas, CA (US)

( * ) Notice: Subject to any disclaimer, the term of this patent is extended or adjusted under 35 U.S.C. 154(b) by 304 days.

(21) Appl. No.: 13/108,892

(22) Filed: May 16, 2011

(65) Prior Publication Data

US 2011/0310388 A1 Dec. 22, 2011

Related U.S. Application Data

(60) Provisional application No. 61/355,694, filed on Jun. 17, 2010.

(51) Int. Cl.
*G01J 4/00* (2006.01)
*G02B 27/14* (2006.01)
*G01N 21/47* (2006.01)

(52) U.S. Cl.
CPC ............ *G02B 27/141* (2013.01); *G02B 27/145* (2013.01); *G01N 2021/4792* (2013.01); *G01N 21/474* (2013.01); *G01N 21/4788* (2013.01)
USPC .......................................... 356/369; 356/364

(58) Field of Classification Search
USPC .................................................. 356/364–369
See application file for complete search history.

(56) References Cited

U.S. PATENT DOCUMENTS

| | | | |
|---|---|---|---|
| 5,157,324 A * | 10/1992 | Chollet | 324/96 |
| 5,859,424 A | 1/1999 | Norton et al. | |
| 6,252,222 B1 * | 6/2001 | Kasapi et al. | 250/214 R |
| 6,509,983 B1 * | 1/2003 | Klug | 359/35 |
| 6,721,691 B2 * | 4/2004 | Bao et al. | 702/189 |
| 6,778,273 B2 * | 8/2004 | Norton et al. | 356/364 |
| 6,798,511 B1 * | 9/2004 | Zhan et al. | 356/369 |
| 6,891,627 B1 | 5/2005 | Levy et al. | |
| 7,164,145 B2 * | 1/2007 | Shakespeare | 250/559.09 |
| 7,557,934 B2 * | 7/2009 | Hugers | 356/601 |
| 2004/0046959 A1 * | 3/2004 | Meeks et al. | 356/369 |
| 2008/0316495 A1 * | 12/2008 | Hirata et al. | 356/491 |
| 2009/0174883 A1 * | 7/2009 | Zawaideh et al. | 356/369 |
| 2009/0279079 A1 | 11/2009 | Shibata et al. | |
| 2011/0069312 A1 * | 3/2011 | Kandel et al. | 356/369 |

OTHER PUBLICATIONS

Shimazu et al. Journal of Lightwave Technology, vol. LT-5, No. 12, Dec. 1987. pp. 1742-1747.*
International Search Report and Written Opinion for PCT/US2011/040389 mailed Feb. 17, 2012.
International Preliminary Report on Patentability for PCT/US2011/040389 mailed Dec. 19, 2012.
Office Action for Taiwan Patent Application No. 100121099 mailed Mar. 19, 2014.

* cited by examiner

*Primary Examiner* — Tarifur Chowdhury
*Assistant Examiner* — Hina F Ayub
(74) *Attorney, Agent, or Firm* — Ann Marie Mewherter

(57) ABSTRACT

Systems and methods for discrete polarization scatterometry are provided.

35 Claims, 6 Drawing Sheets

DISCRETE POLARIZATION SCATTEROMETRY

CROSS-REFERENCE TO RELATED APPLICATIONS

This application claims priority to U.S. Patent Application Ser. No. 61/355,694 entitled "Discrete Polarization Permutation Angular Scatterometer," filed Jun. 17, 2010, which is incorporated by reference as if fully set forth herein.

BACKGROUND OF THE INVENTION

1. Field of the Invention

The present invention generally relates to discrete polarization scatterometry.

2. Description of the Related Art

The following description and examples are not admitted to be prior art by virtue of their inclusion in this section.

Metrology processes are performed on wafers at various points in a semiconductor manufacturing process to determine a variety of characteristics of the wafers such as a width of a patterned structure on the wafer, a thickness of a film formed on the water, and overlay of patterned structures on one layer of the wafer with respect to patterned structures on another layer of the wafer. Optical critical dimension (CD) and overlay metrology are currently performed using either spectroscopic scatterometry or angle-resolved scatterometry.

Some scatterometers collect information by rotating a polarizer and/or analyzer. There are several known techniques for switching between two orthogonally-oriented linear illumination polarizations such as: 1) rotating a linearly polarizing component located in the illumination path by 90 degrees; 2) rotating a half-wave retarder in the illumination path by 45 degrees; and 3) using an electro-optical device such as a Pockels cell or liquid crystal to impose a half-wave of retardation. In addition, there are several techniques for switching between two orthogonally-oriented collection polarizations including: 1) rotating a linearly polarizing component located in the collection path by 90 degrees; 2) rotating a half-wave retarder located in the collection path by 45 degrees, which is followed by a stationary linearly-polarizing component; and 3) using an electro-optical device such as a Pockels cell or liquid crystal to impose a half-wave of retardation, which is followed by a stationary linearly-polarizing component.

Alternatively, previously used architectures separate illumination and collection paths with a non-polarizing beam splitter (non-PBS). One example of such a sensor architecture is shown in FIG. 1. In particular, FIG. 1 illustrates one example of a previously used rotating polarizer scatterometer. As shown in FIG. 1, the scatterometer includes illumination optics 10 configured to direct light to polarizing component 12, which may be a rotating polarizer. Light from polarizing component 12 is directed to non-PBS 14, which directs the light to objective lens 16. Objective lens 16 directs the light to wafer 18. Light scattered from wafer 18 is collected by objective lens 16 and directed by non-PBS 14 to polarizing component 20. Polarizing component 20 may be a rotating analyzer. Light exiting polarizing component 20 is directed to collection optics 22.

There are several disadvantages to the above-described scatterometers. For example, rotating optical components is relatively slow. In addition, precisely rotating optical components can be difficult. Furthermore, non-repeatability in the rotation of optical components can degrade system calibrations. Using separate optical components to establish illumination and collection polarizations also makes precise alignment of the collection and illumination polarization axes difficult. In addition, the polarization purity of half-wave plates and electro-optical retarders such as Pockels cells and liquid crystals is poor. Switching lasers on and off electronically also reduces stability and repeatability.

Accordingly, it would be advantageous to develop scatterometers that overcome the shortcomings of speed of measurement and ease and stability of calibration inherent in previously used architectures without reducing the information content generated by continuous motion polarizing instruments such as rotating polarizer and rotating analyzer scatterometers.

SUMMARY OF THE INVENTION

The following description of various embodiments is not to be construed in any way as limiting the subject matter of the appended claims.

One embodiment relates to an optical subsystem of a scatterometer. The optical subsystem includes one or more light sources configured to produce light having different polarizations. The optical subsystem also includes a polarizing beam splitter configured to separate the light into two different light beams having orthogonal and mutually exclusive polarizations. In addition, the optical subsystem includes two or more first optical elements configured to direct the two different light beams to a wafer. The optical subsystem further includes one or more second optical elements configured to control which one of the two different light beams illuminates the wafer during measurements. The optical subsystem also includes a detection subsystem configured to separately detect two different scattered light beams resulting from illumination of the wafer with the one of the two different light beams and to separately generate output responsive to the two different scattered light beams. The two different scattered light beams have orthogonal and mutually exclusive polarizations. All optical surfaces of the optical subsystem used for the measurements are stationary during the measurements. The optical subsystem and scatterometer may be further configured as described herein.

Another embodiment relates to a scatterometer. The scatterometer includes the elements of the optical subsystem described above. In addition, the scatterometer includes a computer subsystem configured to determine one or more characteristics of features formed on the wafer using the output. The scatterometer may be further configured as described herein.

An additional embodiment relates to a scatterometry method. The method includes producing light having different polarizations. The method also includes separating the light into different light beams having orthogonal and mutually exclusive polarizations. In addition, the method includes directing the two different light beams to a wafer. The method further includes controlling which one of the two different light beams illuminates the wafer during measurements. The method also includes separately detecting two different scattered light beams resulting from illuminating the wafer with the one of the two different light beams. In addition, the method includes separately generating output responsive to the two different scattered light beams. The two different scattered light beams have orthogonal and mutually exclusive polarizations. All optical surfaces used for steps of the method are stationary during the measurements. In addition, the method includes determining a characteristic of features formed on the wafer using the output.

Each of the steps of the method described above may be performed as described further herein. The method described above may include any other step(s) of any other method(s) described herein. The method described above may be performed using any of the systems described herein.

BRIEF DESCRIPTION OF THE DRAWINGS

Further advantages of the present invention will become apparent to those skilled in the art with the benefit of the following detailed description of the preferred embodiments and upon reference to the accompanying drawings in which.

Figure 1:
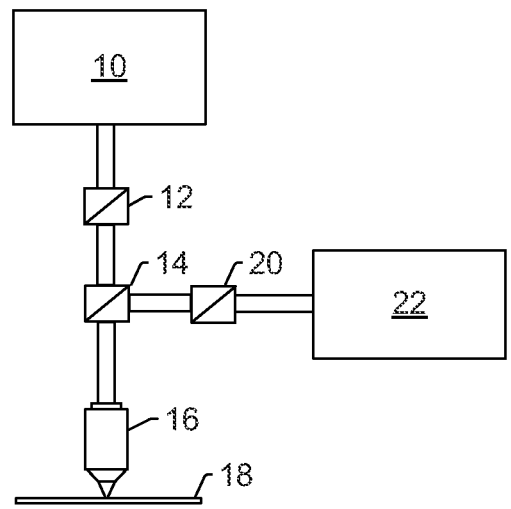
FIG. 1 is a schematic diagram illustrating a side view of one example of a previously used optical subsystem of a scatterometer.

While the invention is susceptible to various modifications and alternative forms, specific embodiments thereof are shown by way of example in the drawings and will be described herein in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

One embodiment relates to an optical subsystem of a scatterometer. The scatterometer is intended for use in various phases of semiconductor or related device production such as lithography and etch. In some embodiments, the scatterometers described herein may be integrated into a semiconductor fabrication system such as a lithography system or an etch system or any other system that alters the wafer physically, chemically, or mechanically in some manner. The scatterometer may be integrated into the semiconductor fabrication system such that the scatterometer can measure the wafer and determine a characteristic of the wafer during a step, before a step, after a step, and/or between steps of a process performed on the wafer by the semiconductor fabrication system without removing the wafer from the semiconductor fabrication system (i.e., while the wafer is disposed within the semiconductor fabrication system). Examples of how the scatterometer may be integrated into a semiconductor fabrication system are described and illustrated commonly owned U.S. Pat. No. 6,891,627 to Levy et al., which is incorporated by reference as if fully set forth herein.

The scatterometers described herein may be used for the measurement of optical and/or structural characteristics of either device or test features during semiconductor manufacture. The optical or structural characteristics include, but are not limited to, critical dimension (CD) such as height, side wall angle, pitch, linewidth, film thickness; refractive indices, and overlay between different layers or between exposures within a single layer. The scatterometers described herein may operate by sampling a discrete set of illumination and collection polarization permutations and subsequently analyzing them by a model based or differential signal metrology approach. In this manner, the scatterometers described herein may be referred to as discrete polarization permutation scatterometers (e.g., angular scatterometers).

Scatterometry and angular optical scatterometry are known methods of CD metrology and are commonly used in semiconductor manufacture. Many sensor architectures utilize polarized illumination and collection to enhance sensitivity and selectivity to particular structural and optical parameters. For a given wavelength, azimuthal incidence angle, and polar incidence angle, a Jones matrix that includes four complex numbers may be used to fully described the scatterometry event from an arbitrary structure. Hence, the maximum achievable scatterometry information is contained in eight illumination and collection polarization permutations. In the embodiments described herein, the set of permutations of polarization states may include, but is not necessarily limited to, all combinations of linearly polarized illumination and collection along the X and Y axes in the plane of the wafer or combinations of radial and polar polarization of the illumination and collection paths.

Figure 2:
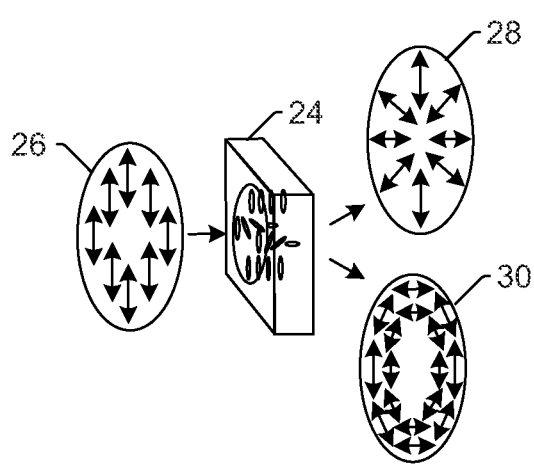
FIG. 2 is a schematic diagram illustrating a side view of one example of a polarization converter that may be used in embodiments described herein.

One example of a radial or polar polarization converter is shown in FIG. 2. In particular, optical element 24 is an example of a linear to radial or azimuthal (polar) polarization converter that may be used in the embodiments described herein and that is commercially available as the ARCoptix Radial-Azimuthal Polarization Converter from ARCoptix, Neuchâtel, Switzerland. As shown in FIG. 2, linearly polarized beam 26 may enter optical element 24 and be converted into either radially polarized beam 28 or azimuthally polarized beam 30.

All optical surfaces of the optical subsystem used for the measurements are stationary during the measurements. For example, as described further herein, the optical subsystem may include one or more elements such as shutters that are configured to be moved into and out of optical path(s) of the optical subsystem. However, any optical elements that are moved, other than for calibration purposes, are not used for measurements. For example, since the shutters block tight from reaching the wafer or a detector, the shutters may prevent measurements but are not actually used for measurements. In this manner, one of the important characteristics of the embodiments described herein is that as opposed to methods based on rotating polarizers and analyzers, the embodiments described herein enable high speed switching between permutations of a discrete set of polarizations without moving any of the optical surfaces in the optical path of the instrument. In this way, systematic errors that are associated with optical calibration drifts are reduced, within a single measurement and over time between measurements, due to the static nature of the optical path.

In one embodiment of the optical subsystem, which may be referred to as a path-based polarization switching architecture, a set of polarization permutations is selected by switching between a finite set of fixed optical paths. Such architecture could be either sequential, parallel, or a combination of both. By sequential, the intention is that each polarization permutation is achieved by following a specific light path between illumination and collection optics. Such sequential switching may be achieved by the insertion or removal of a beam stop or by controlling any other appropriate beam diversion device.

Figure 3:
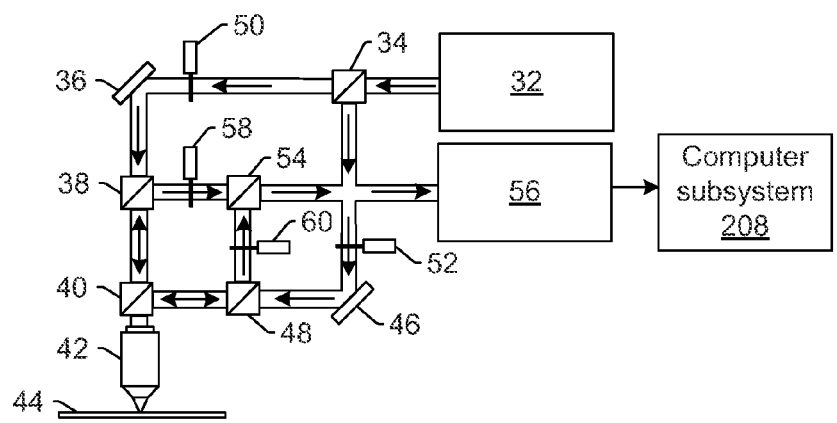
FIG. 3 is a schematic diagram illustrating a side view of one embodiment of an optical subsystem of a scatterometer and one embodiment of a scatterometer.

An embodiment of a path-based discrete polarization sequential or switching scatterometer is shown in FIG. 3. The optical subsystem includes one or more light sources configured to produce light having different polarizations. For example, as shown in FIG. 3, the optical subsystem may include illumination optics 32, which may include one or more light sources. The one or more light sources may include, for example, one or more lasers. The one or more light sources may be further configured as described herein. In addition, illumination optics 32 may be further configured as described herein.

The optical subsystem includes a polarizing beam splitter (PBS) configured to separate the light into two different light beams having orthogonal and mutually exclusive polarizations. The polarizations may be orthogonal horizontal (H) and vertical (V) polarizations, which are defined with respect to a suitably chosen reference plane. For example, as shown in FIG. 3, the light from illumination optics 32 is directed to illumination PBS 34 that is configured to separate the light into two different light beams having orthogonal and mutually exclusive polarizations. In addition, the PBS may split the illumination light into orthogonal linear components. PBS 34 may include any suitable PBS known in the art.

The optical subsystem includes two or more first optical elements configured to direct the two different light beams to a wafer. For example, as shown in FIG. 3, the first optical elements may include reflective element 36, non-PBS 38, PBS 40, reflective element 46, and non-PBS 48. Reflective element 36 is configured to direct one of the light beams from PBS 34 to non-PBS 38, which transmits that beam of light to PBS 40. Reflective element 46 directs the other light beam from PBS 34 to non-PBS 48, which transmits that beam of light to PBS 40. PBS 40 may then direct the two different light beams to wafer 44. In this manner, PBS 40 is a common PBS for both illumination light beams. In particular, the "common" PBS recombines the two illumination polarization paths. Reflective elements 36 and 46 may include any suitable reflective elements such as flat mirrors. Non-PBS's 38 and 48 may include any suitable non-PBS's known in the art. PBS 40 may include any suitable PBS known in the art. In this manner, in one embodiment, the two or more first optical elements include a first non-PBS (e.g., non-PBS 38) and an additional PBS (e.g., PBS 40), both positioned in the path of a first of the two different light beams, and a second non-PBS (e.g., non-PBS 48) and the additional PBS (e.g., PBS 40), both positioned in the path of a second of the two different light beams.

In some embodiments, the optical subsystem includes an objective configured to direct light from the additional PBS to the wafer and to collect light scattered from the wafer, and the light scattered from the wafer is separated into two different scattered light beams by the additional PBS. For example, as shown in FIG. 3, the different light beams may be directed from PBS 40 to objective 42, which focuses the light beams to wafer 44 and collects light scattered from the wafer. Objective 42 (or "objective lens") may include one or more refractive optical elements in any suitable configuration. In this manner, the "common" PBS recombines the two illumination polarization paths just before launching into the objective. PBS 40 then separates the scattered light into two different scattered light beams. For example, the "common" PBS separates the collected scattered light into orthogonal linear components.

The optical subsystem includes one or more second optical elements configured to control which one of the two different light beams illuminates the wafer during measurements. In one embodiment, the one or more second optical elements include a first shutter configured to be positioned in a path of a first of the two different light beams and a second shutter configured to be positioned in a path of a second of the two different light beams. For example, as shown in FIG. 3, the one or more second optical elements may include shutter 50 configured to be positioned in a path of a first of the two different light beams and shutter 52 configured to be positioned in a path of a second of the two different light beams. The shutters may include any suitable shutters known in the art and the optical subsystem and the scatterometer may be configured to move the shutters into and out of the paths of the different light beams in any suitable manner. In this manner, the optical subsystem may include separate shutters on the two illumination paths to block the undesired illumination polarization from reaching the wafer. The one or more second optical elements may, therefore, be configured to control which light beam illuminates the wafer by blocking. However, the one or more second optical elements may be configured to control which light beam illuminates the wafer by refraction, diffraction, or in any other manner. For example, as described further herein, the one or more second optical elements may include acousto-optical deflectors (AODs) that can be used to divert a light beam from an optical path depending on which light beam is to be used for measurements.

In one embodiment, the scatterometer is configured to control the one or more second optical elements such that the two different light beams illuminate the wafer sequentially one at a time. For example, the scatterometer may be configured to position shutter 50 in the path of the first of the two different light beams and shutter 52 out of the path of the second of the two different light beams white the second of the two different light beams is used to illuminate the wafer for measurements. Then, the scatterometer may be configured to switch the positions of the shutters so that the first of the two different light beams can illuminate the wafer for measurements. The scatterometer may be configured to control and alter the positions of the shutters in any suitable manner (e.g., using any suitable control subsystem (not shown) known in the art).

The optical subsystem includes a detection subsystem configured to separately detect two different scattered light beams resulting from illumination of the wafer with the one of the two different light beams and to separately generate output responsive to the two different scattered light beams. The two different scattered light beams have orthogonal and mutually exclusive polarizations. For example, as shown in FIG. 3, light scattered from the wafer may be collected by objective 42 and then separated by PBS 40 into two different scattered light beams having orthogonal and mutually exclusive polarizations. In this manner, PBS 40 is a common PBS for both scattered light beams. One of the scattered light beams may be directed to non-PBS 38, which may direct that light beam to PBS 54. In this manner, non-PBS 38 separates that scattered light beam from the illumination path. PBS 54 allows that scattered light beam to pass to collection optics 56. In addition, the other scattered light beam may be directed to non-PBS 48, which may direct that light beam to PBS 54 thereby separating that collected scattered light beam from the illumination path. PBS 54 reflects that light beam to collection optics 56. In this manner, PBS 54 is a "collection PBS" that recombines the two collection polarization paths before sending the collected light to the collection optics and measurement sensor. The collection optics may be configured as described further herein. PBS 54 may include any suitable PBS known in the art.

In one embodiment, the detection subsystem is configured such that the two different scattered light beams travel along optical paths along which the two different light beams used to illuminate the wafer travel. For example, as shown in FIG. 3, the collected scattered light beams and the two different illumination light beams may travel along the same optical paths between PBS 40 and non-PBS 38 and PBS 40 and non-PBS 48.

In some embodiments, the detection subsystem is configured to detect the two different scattered light beams sequentially. For example, in one embodiment, the detection substem includes a first shutter configured to be positioned in a path of a first of the two different scattered light beams and a second shutter configured to be positioned in a path of a second of the two different scattered light beams, and the first and second shutters control which of the two different scattered light beams reaches a detector of the detection subsystem. In this manner, separate shutters on the two collection paths block the undesired linear collection polarization from reaching the measurement sensor. The detection subsystem may, therefore, be configured to control which light beam is detected by blocking. However, the detection subsystem may be configured to control which light beam is detected by refraction, diffraction, or in any other manner. For example, the detection subsystem may include AODs that can be used to divert a light beam from an optical path depending on which light beam is to be detected.

In one such embodiment, as shown in FIG. 3, the detection subsystem may include two shutters 58 and 60, each of which may be positioned in the path of one of the scattered light beams. In particular, shutter 58 may be positioned in the path of one scattered light beam between non-PBS 38 and PBS 54, and shutter 60 may be positioned in the path of the other scattered light beam between non-PBS 48 and PBS 54. In this manner, one shutter can be placed in the path of one of the scattered light beams while the other scattered light beam is being detected by the detection subsystem and vice versa. The shutters may include any suitable shutters known in the art and the optical subsystem and the scatterometer may be configured to move the shutters into and out of the paths of the different scattered light beams in any suitable manner. In addition, the shutters may be replaced by other beam diverting optical elements described herein. As such, the detection subsystem may include only one detector that is used to sequentially and separately detect the two different scattered light beams. The detector may include any suitable detector. The optical subsystem shown in FIG. 3 may be further configured as described herein.

Figure 4:
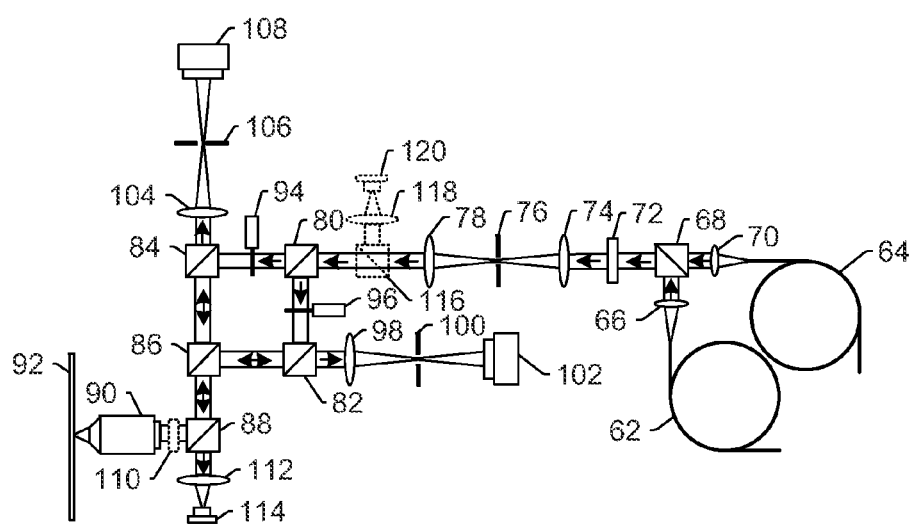
FIGS. 4-10 are schematic diagrams illustrating side views of various embodiments of an optical subsystem or portions of an optical subsystem of a scatterometer.

An alternative to the above architecture is a path-based parallel discrete polarization scatterometer. Use of the term "parallel" in this context refers to a system that acquires a subset of polarization permutations by the use of, for example, a PBS in the collection path of the instrument, which allows at least two polarization states to be collected simultaneously on different collection channels. One embodiment of an architecture of a path-based discrete polarization parallel scatterometer is shown in FIG. 4. In this embodiment, the detection subsystem is configured to separately detect the two different scattered light beams simultaneously. For example, in one embodiment described further herein, the detection subsystem is configured to direct the two different scattered light beams to two different detectors simultaneously.

As shown in FIG. 4, the optical subsystem includes two optical fibers 62 and 64. Each of the optical fibers may be coupled to a light source (not shown in FIG. 4) that is configured to provide light having a different polarization. For example, optical fiber 62 may be coupled to a first light source (not shown in FIG. 4) configured to provide light having a first polarization, and optical fiber 64 may be coupled to a second light source (not shown in FIG. 4) configured to provide light having a second polarization that is orthogonal to and mutually exclusive of the first polarization. Optical fibers 62 and 64 may be further configured as described herein. In this manner, light exiting the two optical fibers may have orthogonal and mutually exclusive polarizations. Light from fiber 62 may be imaged by refractive optical element 66 to PBS 68. In addition, light from fiber 64 may be imaged by refractive optical element 70 to PBS 68. PBS 68 is configured to reflect light from fiber 62 and transmit light from fiber 64 such that light having both polarizations is directed along a common optical path.

Light from PBS 68 may be directed to apodizer 72. Light from apodizer 72 may be directed to refractive optical element 74, which focuses the light through illumination field stop (IFS) 76. Light that passes through IFS 76 may be imaged by refractive optical element 78 to PBS 80. PBS 80 is configured to separate the light into two different light beams having orthogonal and mutually exclusive polarizations. For example, light having one polarization is reflected by PBS 80 to non-PBS 82, while light having an orthogonal and mutually exclusive polarization is transmitted by PBS 80 to non-PBS 84.

Non-PBS's 82 and 84 reflect the light from PBS 80 to PBS 86, which directs the light beams to non-PBS 88. Non-PBS 88 reflects the light from PBS 86 to objective 90, which focuses the light to wafer 92. In this embodiment, therefore, the two or more first optical elements that are configured to direct the two different light beams to a wafer include non-PBS's 82, 84, and 88 and PBS 86.

The one or more second optical elements configured to control which one of the two different light beams illuminates the wafer during the measurements in this embodiment include shutters 94 and 96, which may be further configured as described herein. In particular, when light reflected by PBS 80 is to be used for measurements, shutter 94 may be positioned in the optical path between PBS 80 and non-PBS 84, and when light transmitted by PBS 80 is to be used for measurements, shutter 96 may be positioned in the optical path between PBS 80 and non-PBS 82.

Light scattered from the wafer is collected by objective 90 and is directed to non-PBS 88, which reflects the light to PBS 86. PBS 86 separates the light into two different scattered light beams having orthogonal and mutually exclusive polarizations. The scattered light beam reflected by PBS 86 is directed through non-PBS 82 and is focused by refractive optical element 98 through collection field stop (CFS) 100. Light that passes through CFS 100 is detected by detector 102 of the detection subsystem. The scattered light beam transmitted by PBS 86 is directed through non-PBS 84 and is focused by refractive optical element 104 through CFS 106. Light that passes through CFS 106 is detected by detector 108 of the detection subsystem. The detectors may be charge coupled devices (CCDs). In this manner, scattered light beams having orthogonal and mutually exclusive polarizations may be separated by common PBS 86 and directed to different detectors, which may separately detect the different scattered light beams simultaneously. Each of the elements of the optical subsystem shown in FIG. 4 may include any suitable optical elements. In addition, the optical subsystem shown in FIG. 4 may be further configured as described herein.

In either case described above, the scatterometer could in principle be spectroscopic or angle resolved, although particular attention will be paid to the angle resolved architecture in the description below. An additional feature is the use of specialized combined beam splitters (not shown) in the embodiments described herein. The specialized combined beam splitters could be formed by merging the external planar surfaces of two adjacent beam splitters in order to eliminate scatter and ghosts and to improve alignment and polarization purity. For example, a specialized combined beam splitter can be formed by using continuous glass between common PBS 86 and non-PBS 88 shown in FIG. 4. Such a beam splitter would eliminate two glass-to-air interfaces and all of the problematic scatter and ghost reflections associated with these interfaces. Such a configuration also allows alignment of the S and P axes of the combined beam splitter during manufacture instead of on the optical bench.

In one embodiment, the illumination used in the embodiments described herein is azimuthally symmetric illumination although this is by no means a limitation on the embodiments described herein. For example, an apodized azimuthally symmetric illumination source may be used in the embodiments described herein. Such an apodization scheme is described in commonly owned U.S. Pat. No. 5,858, 424 to Norton et al. and commonly owned U.S. Patent Application Publication No. 2011/0069312 by Kandel et al. published on Mar. 24, 2011, both of which are incorporated by reference as if fully set forth herein. Such an illumination architecture enables an exceedingly small measurement spot size on the wafer. Furthermore, if the objective is chosen to be in an infinite conjugate condition, a highly collimated beam will be produced in the optical path of the instrument between the objective and the collection optics. This configuration further enables a number of optional architectural advantages which are described further herein.

In one embodiment, the optical subsystem includes a waveplate positioned between the objective and the additional PBS. For example, another possible option is the insertion of a quarter waveplate in the optical column in the vicinity of the objective. In one such example, as shown in FIG. 4, waveplate 110 may be inserted in the optical path between objective 90 and non-PBS 88. This waveplate can enable the detection of additional cross-polarization Jones matrix terms through the addition of phase information.

Another option is that, to eliminate the two shutters, the angle of polarization can be directly controlled to null the signal on a monitor sensor at the back of the non-PBS. For example, as shown in FIG. 4, light that is transmitted by non-PBS 88 may be focused by refractive optical element 112 to monitor sensor 114. The angle of polarization of the light may be controlled until the output generated by monitor sensor 114 is nulled. In a different example, non-PBS 116 may be positioned in the illumination path and configured to separate a portion of both of the different illumination light beams from the illumination path. The separated portions of the different light beams may be directed to refractive optical element 118, which may focus the different light beams to monitor sensor 120. The angle of polarization of the light may be controlled until the output generated by monitor sensor 120 is nulled.

An alternative architecture that may be used in embodiments described herein and that can enable access to phase information is the Linnik interferometer architecture. Such an architecture can be enabled by replacement of the monitor sensor with an additional objective lens and a mirror in its focal plane. Such an optical architecture may be further enhanced by scanning through a moderately small angle with structured illumination. It can be two-dimensional and optimized to a feature on the wafer.

A number of more detailed illuminator architectures will now be described. Features of these architectures may be further arbitrarily combined. Each of these architectures can be advantageously combined with discrete polarization permutation scatterometers as will be described below.

Figure 5:
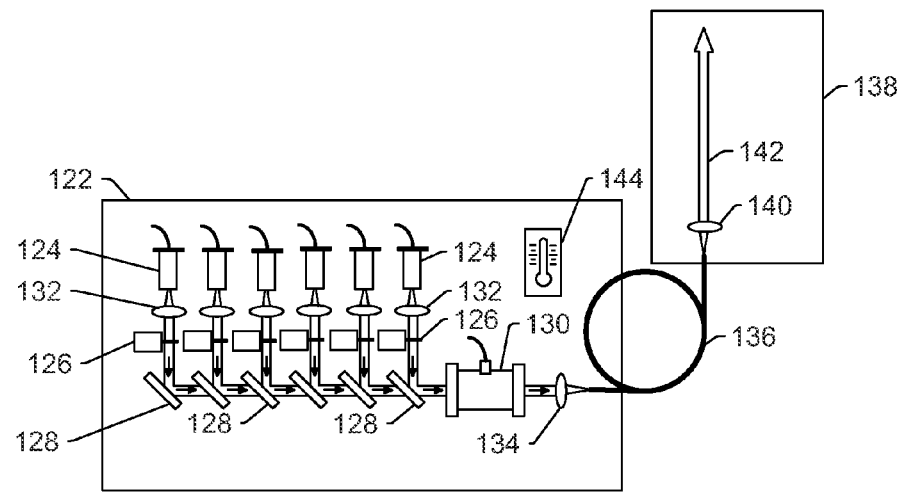

In one embodiment, the one or more light sources include two or more lasers, each configured to generate a different wavelength of light, a shutter and a dichroic combiner are coupled to each of the two or more lasers, and light from the dichroic combiners is directed to a Pockels cell before being directed to the PBS. One such embodiment of a Pockels cell-based multi-wavelength illuminator is shown in FIG. 5. In this embodiment, source optics 122 include a number of discrete laser light sources 124 that are coupled via shutters 126 and dichroic combiners 128 into Pockels cell 130, which provides polarization and intensity control by rotating the polarization state at the entrance to a PBS (not shown in FIG. 5) without significant toss of energy. The PBS may be an illumination PBS such as that shown in FIG. 3. The wavelengths of the light produced by the light sources may span the visible and near infrared spectrum, but this is not a limitation. As shown in FIG. 5, light from each of the light sources may be directed by refractive optical elements 132 to dichroic combiners 128 when the shutter coupled to each of the light sources is not positioned in the path of the light from the light sources. Light from the Pockels cell may be focused by refractive optical element 134 to optical fiber 136, typically single-mode, that propagates both polarization states (e.g., H and V) to bench optics 138, which may include refractive optical element 140 configured to direct light 142 to other elements of the optical subsystem described herein. For example, light from the optical fiber may be directed to a shutter positioned after an apodizer, and the shutter may select illumination polarization on the optical bench. By separating the illuminator from the main optical bench, heat and vibration from the lasers and shutters are isolated from the main optical bench. In addition, the source optics may include temperature control subsystem 144, which may have any suitable configuration, configured to control the temperature in the source optics. Furthermore, wavefront disruptions, scatter, and ghosts from beam combining, intensity control, and polarization switching functions are all filtered out by the single-mode polarization maintaining (PM) fiber which provides a clean mode structure at the entry to the apodizer or other elements of the optical subsystem. Each of the elements shown in FIG. 5 may include any suitable commercially available element.

Figure 6:
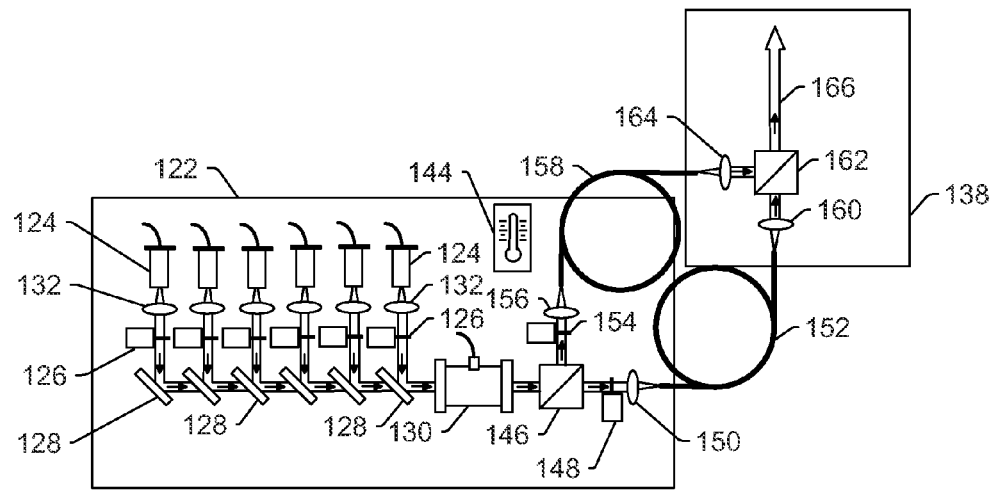

FIG. 6 illustrates a Pockels cell-based multi-wavelength illuminator with an additional PBS. In this embodiment, multiple lasers are combined and polarization and intensity is controlled as in the embodiment shown in FIG. 5. However, in this embodiment, a PBS is placed in the optical path and shutters select wavelength and polarization (e.g., H or V linear polarization) at the entry point into two single mode fibers. For example, light from Pockels cell 130 may be directed to PBS 146, which splits the light into different light beams having orthogonal and mutually exclusive polarizations. Light having a first polarization may be directed to shutter 148 if positioned in the path of the light or to refractive optical element 150, which focuses the light to optical fiber 152. Light having a second polarization, orthogonal to and mutually exclusive of the first polarization, may be directed to shutter 154 if positioned in the path of the light or to refractive optical element 156, which focuses the light to optical fiber 158. In this manner, shutters 148 and 154 may control which of the different light beams is used for illumination of the wafer during measurements. Light from optical fibers 152 and 158 may be directed to bench optics 138, which in this embodiment may include refractive optical element 160 configured to direct light from optical fiber 152 to PBS 162 and refractive optical element 164 configured to direct light from optical fiber 158 to PBS 162. Light 166 exiting PBS 162 may then be directed to other elements of the optical subsystem described herein such as an apodizer (not shown in FIG. 6). Each of the elements shown in FIG. 6 may include any suitable commercially available elements.

Figure 7:
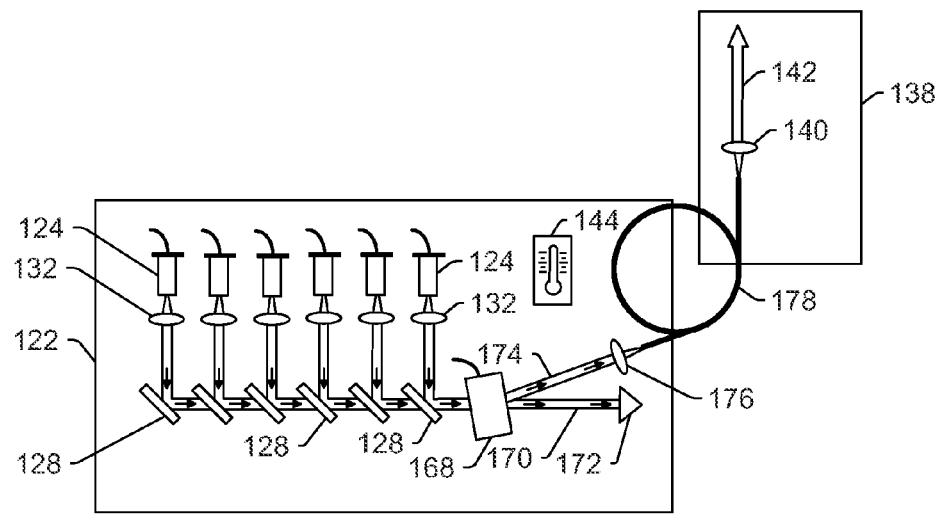

In another embodiment, the one or more light sources include two or more lasers, each configured to generate a different wavelength of tight, a dichroic combiner is coupled to each of the two or more lasers, and light from the dichroic combiners is directed to an AOD before being directed to the PBS. One such embodiment of an acousto-optical beam combiner illuminator architecture is shown in FIG. 7. For example, as shown in this figure, acousto-optic beam combiner 168 is used to switch the light source between lasers by modification of drive frequency which controls diffraction angle, i.e., wavelength, thereby obviating the need for a shutter on each laser. This configuration also enables intensity modulation by modifying the diffraction efficiency which is dependent on the piezoelectric transducer (PZT) modulation intensity sending zero order tight 170 to light dump 172. First order light 174 may be focused by refractive optical element 176 to optical fiber 178, which may direct the tight to bench optics 138, which may be configured as described herein. Furthermore, if the light source is linearly polarized and oriented at 45 degrees, shutters after the apodizer may select illumination polarization. Such an architecture allows extremely fast wavelength switching and lowers cost by removal of shutters and beam splitters. Each of the elements shown in FIG. 7 may include any suitable commercially available elements.

Figure 8:
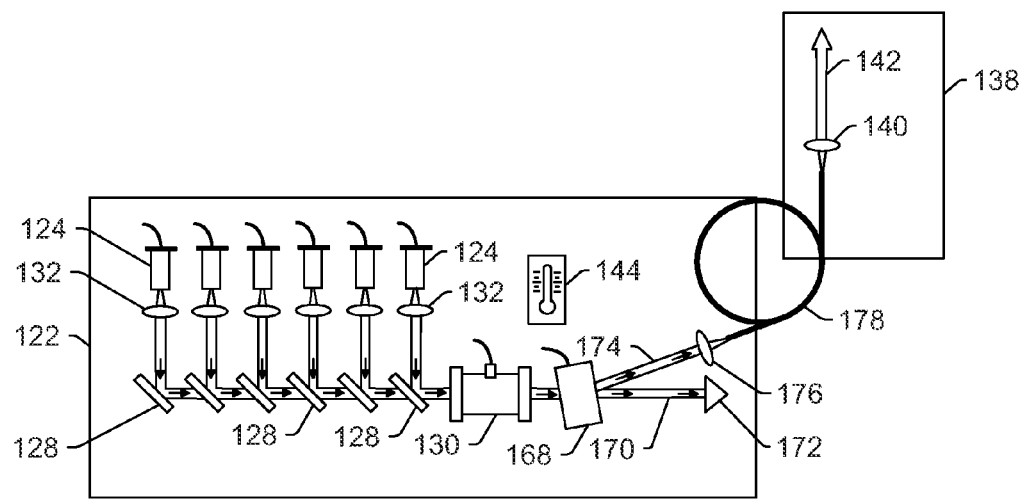

In an embodiment, the optical subsystem includes a Pockels cell positioned between the dichroic combiners and the AOD. One embodiment of an acousto-optic and Pockels cell illuminator configuration is shown in FIG. 8. As shown in this figure, Pockels cell 130 is re-introduced into the embodiment shown in FIG. 7 between beam combiners 128 and AOD 168. The Pockels cell improves light throughput since polarization can be arbitrarily rotated without energy loss. Each of the elements shown in FIG. 8 may include any suitable commercially available elements.

Figure 9:
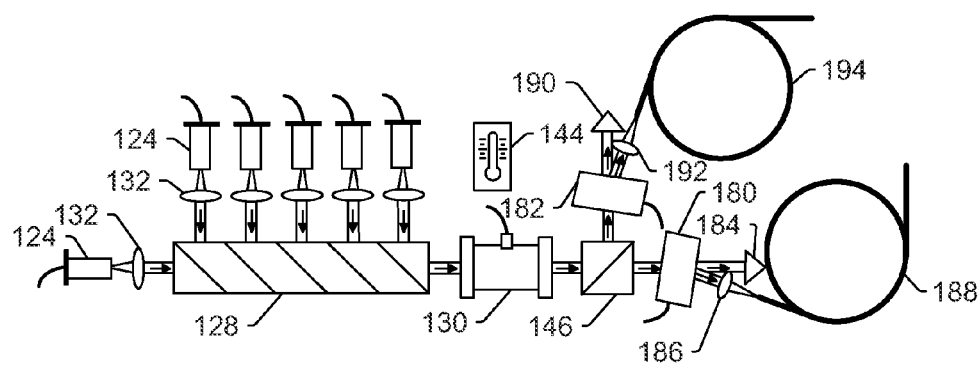

In one embodiment, the one or more light sources include two or more lasers, each configured to generate a different wavelength of light, dichroic combiner is coupled to each of the two or more lasers, light from the dichroic combiners is directed to a Pockels cell before being directed to the PBS, and the one or more second optical elements include two AODs. One such embodiment of an illuminator architecture with dual AODs enabling fast wavelength and polarization switching is shown in FIG. 9. For example, as shown in FIG. 9, Pockels cell 130 may rotate polarization to control intensities on the two different polarization (e.g., H and V) paths while AODs 180 and 182 are used independently for each polarization. The drive frequency of the AODs controls diffraction angle to select wavelength and to effectively shutter the different polarization paths. As described above, zero order light from AOD 180 may be directed to beam dump 184 while first order tight from the AOD may be focused by refractive optical element 186 to optical fiber 188. Light exiting optical fiber 188 may be directed to the bench optics as described above. Similarly, zero order light from AOD 182 may be directed to beam dump 190 while first order light from this AOD may be focused by refractive optical element 192 to optical fiber 194. Light exiting optical fiber 194 may be directed to the bench optics as described above. This configuration enables faster wavelength and polarization switching with no moving parts resulting in improved reliability and lower heat load. Each of the elements shown in FIG. 9 may include any suitable commercially available elements.

In another embodiment, any of the illumination subsystem embodiments described herein may be coupled to the scatterometer optical bench by free space optics as opposed to the optical fibers described above.

Figure 10:
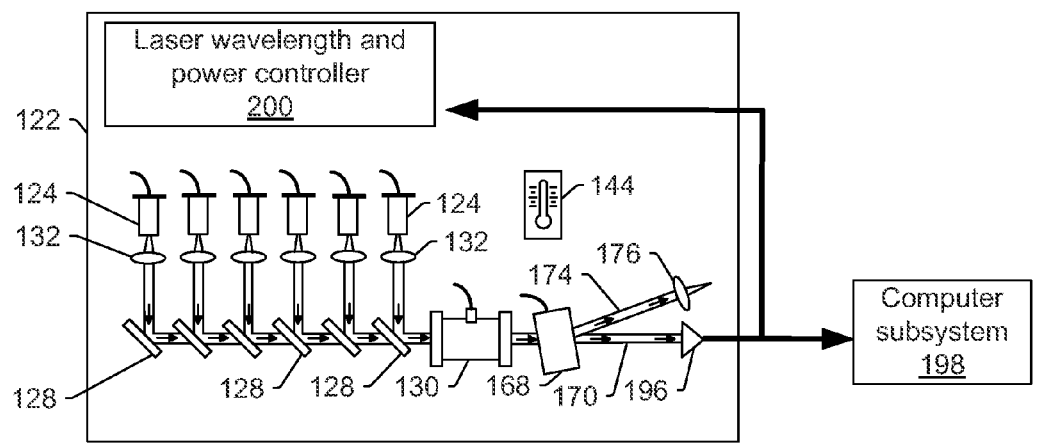

In one embodiment, the optical subsystem includes a control subsystem configured to control one or more wavelengths of the light produced by the one or more light sources. For example, in CD metrology, due to the high sensitivity to wavelength of modeled parameters such as side wall angle, spectral stability is more important than intensity stability. In one such example, a 10 pm shift in center wavelength of the laser line can be significant. This stability is particularly important on stacks where there is low sensitivity to geometrical or optical parameters since there is the risk of misinterpretation of a small change in wavelength as a large change in geometric parameters. In order to deal with this problem, single mode and single wavelength light sources such as diode pumped lasers with a specific set of wavelengths may be used. By monitoring and feedback, substantially high wavelength stability may be achieved. An embodiment of a control methodology is shown in FIG. 10 in which the exact laser wavelength is measured to a substantially high degree of accuracy, for example, parts of a picometer, and this information is fed back to the laser for closed loop wavelength control. Additionally, implementation of such a sensor in the illuminator can detect whether the laser is in single or multimode and assist in the avoidance of mode hopping. An example of an accurate wavelength metrology technique which could be used is that of a Fizeau Etalon. An example of such a laser wavelength metrology system is the 821 series laser wavelength meter, which is commercially available from Bristol Instruments, New York. In a further embodiment, an additional use for this precise wavelength metrology is proposed. Instead of using this metrology to stabilize the laser wavelength at a predetermined wavelength, the wavelength is actually scanned over a restricted wavelength range by, for example, current control of the laser. Other wavelength scanning methods that could be implemented are by temperature control or by mechanical strain with a PZT and by modulation, for example, by modulating the laser cavity in the 1 GHz to 10 GHz range. The exact wavelength is measured by the wavelength metrology system and fedforward to the scatterometer computer subsystem. As far as the location of such a wavelength sensor is concerned, one possible option could be to place it at the location of the beam dump of the AOD shown in FIGS. 7 and 8. For example, in the embodiment of laser wavelength monitoring, stabilization, and feedforward architecture shown in FIG. 10, zero order beam 170 from AOD 168 may be directed to wavelength metrology sensor 196, which may be, for example, a Fizeau Etalon. Output generated by the sensor may be provided to computer subsystem 198, which may be further configured as described herein for scatterometry metrology, such that the computer subsystem may use the output to determine one or more characteristics of one or more features formed on a wafer.

Output generated by the sensor may also be provided to laser wavelength and power controller 200, which may be a computer subsystem configured to control one or more parameters of one or more of light sources 124 based on the output of the sensor. Further advantages of extreme wavelength stability is in wavelength matching between toots and reduction in the modeling library size. Each of the elements shown in FIG. 10 may include any suitable commercially available elements.

On the collection side, a number of alternative architectures may be implemented in the embodiments described herein. In one embodiment, an image sensor is located the pupil plane to allow an image to be collected of the scatterometric pupil function.

In an enhancement of the above embodiment, and in the case when the structure to be measured is periodic with appropriate periodicity and conditional to appropriate restrictions in the illumination numerical aperture (NA), the resultant diffraction orders will be separated in the pupil plane of the collection optics. In the case of non-zero order diffraction, this architecture may allow partial spectral separation in the pupil domain. Furthermore, in the case when the illumination is through a relatively narrow range of angles on the wafer, i.e. relatively low NA illumination, then the spot size on the water will be proportionally increased. For target structures with relatively large pitches, e.g., between 0.4 microns and 2 microns, this spot size increase enables the illumination of multiple cycles of the target structure. Such illumination is advantageous as it allows the collected diffraction orders in the pupil image to be relatively localized and non-overlapping such that their angular location and shape contain information which can be used in the modeling procedure to predict the target characteristics. Such a method can be further enhanced by insertion, in the illumination pupil where the apodizer is currently located, of a multiple pole aperture, such as a dipole or quadrupole aperture. Such a structured illumination architecture can also be achieved by insertion of a diffractive optical element in the illumination column.

As mentioned above, in the case of an infinite conjugate architecture resulting in a well collimated beam between illumination optics, objective lens, and collection optics, the pupil plane is easily accessible and this allows the option of placing a polarization structure in the pupil (e.g., by insertion of either radial or polar polarizers in the optical column). Additionally, an infinite conjugate architecture combined with a relatively small spot enables a highly collimated beam thereby minimizing vignetting.

Figure 11:
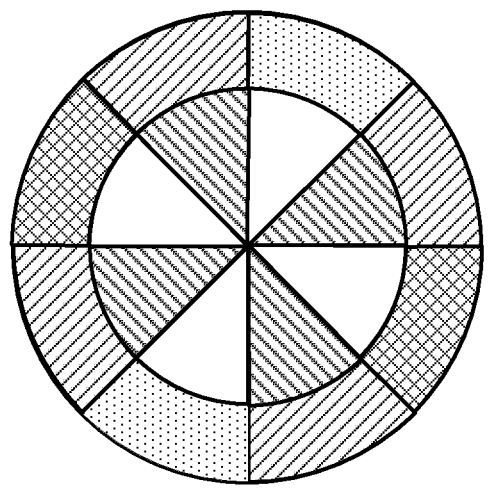
FIG. 11 is a schematic diagram illustrating a side view of one embodiment of a pupil conjugate filter.

In another embodiment, the optical subsystem includes a pupil conjugate filter positioned in the pupil plane of the optical subsystem, and characteristics of the pupil conjugate filter vary as a function of location across the pupil conjugate filter. For example, for the case of an architecture with access to the pupil plane such as those described above, a dedicated pupil conjugate filter may be inserted, with spatially dependent characteristics. Examples of the spatial dependence include spatially dependent wavelength transmission, spatially dependent polarization transmission, spatially dependent phase retardation, and combinations thereof. An example of such a filter is shown in FIG. 11. In this example of a spatially dependent pupil filter, different combinations of spectral filters and polarizations are represented by different fill patterns.

Such an architecture could be utilized to achieve illumination/collection symmetry. In the particular case of a zero order system, an illumination pupil point is reflected to a collection pupil point with the same radial distance and azimuthal angle, but shifted 180 degrees relative to the corresponding illuminating point. Illumination and collection points should enable similar wavelengths to pass. A certain pupil point can be made to pass a multitude of wavelengths. Illumination and collection points could have similar or orthogonal polarizations based on measurement configuration. Two filters can be positioned, one in the illumination side and one in the collection side. Furthermore, the spatial varying filter can be made (or made by parts) using a birefringent material, in which case the phase retardation per pupil point may be controlled by the thickness of the filter. This configuration enables polarization state manipulation per pupil point. Being a relatively low NA configuration in the pupil plane, the fitters can be located with relatively loose tolerances and in several locations.

Figure 12:
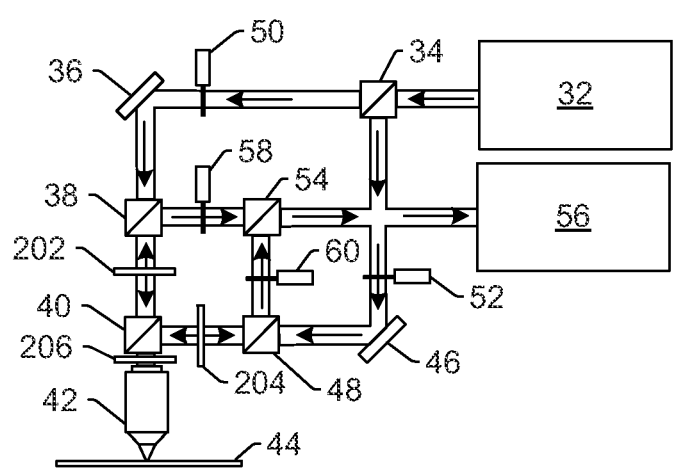
FIG. 12 is a schematic diagram illustrating a side view of another embodiment of an optical subsystem of a scatterometer.

An embodiment of the filter insertion options for such an architecture is shown in FIG. 12. In particular, FIG. 12 shows possible options for filter positioning for polarization, retardation, or spectral pupil control. For example, as shown in FIG. 12, filter 202 may be positioned in the optical path between non-PBS 38 and PBS 40, filter 204 may be positioned in the optical path between non-PBS 48 and PBS 40, and filter 206 may be positioned in the optical path between PBS 40 and objective 42.

In some embodiments, the measurements include angle-resolved scatterometry measurements. Such measurements may be performed as described further herein. In a further embodiment, the measurements include multiple wavelength scatterometry measurements. For example, the detection side optical architecture may be spectroscopic in addition to or instead of angle-resolved. In this case, a spectrometer (not shown) may be integrated into the collection optics, and the spectral dependence of the scatterometric signal may be collected for each one of the different polarization permutations that are sequentially or simultaneously measured.

The detection side optical architecture is also not limited to angle-resolved or spectroscopic measurements. For example, combined measurements from different wavelengths and angles are also possible. Such measurements can be achieved in many ways. For example, several areas of the pupil can be imaged onto the entrance slits of several independent spectrometers, thus obtaining full spectral information for the several angles which correspond to the selected pupil areas. The selected pupil areas can also be coupled to the spectrometers by fibers instead of being imaged onto the spectrometers. Another possibility is to obtain more detailed angular information by using a spot-to-line fiber bundle, coupling an image of the pupil to an imaging spectrometer, mapping the two-dimensional pupil onto the imaging direction of the spectrometer. The second direction of the spectrometer is of course used to obtain spectral information for each point of the imaging direction.

Another embodiment relates to a scatterometer. The scatterometer includes the elements of the optical subsystem described above. The scatterometer also includes a computer subsystem configured to determine one or more characteristics of features formed on the wafer using the output. For example, as shown in FIG. 3, the scatterometer includes computer subsystem 208 that is configured to determine one or more characteristics of features on the wafer using the output generated by the detection subsystem. In this manner, the computer subsystem may be configured to use output from the detection subsystem responsive to scattered tight to determine characteristic(s) of the features. The computer subsystem may determine the characteristic(s) using any suitable method(s), algorithm(s), model(s), technique(s), etc. known in the art.

Computer subsystem 208 is coupled to the detection subsystem (e.g., by one or more transmission media, which may include any suitable transmission media known in the art) such that the computer subsystem may receive the output generated by the detection subsystem. Computer subsystem 208 may take various forms, including a personal computer system, mainframe computer system, workstation, system computer, image computer, programmable image computer, parallel processor, or any other device known in the art. In general, the term "computer system" may be broadly defined to encompass any device having one or more processors, which executes instructions from a memory medium.

The optical architectures described herein are advantageous for the measurement of differential-signal scatterometry overlay (SCOL). In this case, the metrology target may include several cells, each having at least two patterns between which overlay is measured. The two patterns may be in the same layer or in different layers. The geometrical designs of the cells (pattern pitch, CD, etc) are identical, except for a programmed offset between the two patterns, which varies from cell to cell. A scatterometry signal is measured from each cell, and then differences between signals are calculated, from which the value of the overlay is extracted. The advantage of this method over standard scatterometry CD methodologies, is that the measurement of the overlay relies on symmetry rather than a detailed comparison with simulated signals. As a result, no regression on or generation of a large library of simulated signals is required.

The disadvantage of SCOL is the relatively large size of the target, which includes several cells. As an example, an SCOL target may include eight cells, four for X-overlay measurement and four for Y-overlay. The architectures described herein allow multiple measurements on each cell in specific ways, which enable the extraction of one or more differential signals from each cell, instead of a differential signal from a pair of cells in the standard method. Enabling such measurements reduces the number of cells per target and hence the size of the target. In addition, the relatively small illumination spot allows measurements of significantly smaller cells (e.g., 5 micron or smaller), further reducing target size.

As an example of multiple measurements from each cell of an SCOL target, consider the case in which two signals are measured from each cell such that the difference between these signals is an anti-symmetric function of the offset between the two patterns:

$$\Delta S(\text{offset}) = -\Delta S(-\text{offset})$$

Such an anti-symmetric differential signal vanishes at offset zero and is linear in the offset for relatively small values of the offset. The slope of this linear function along with the overlay can be determined from measurements on two cells with different, relatively small programmed offsets (two measured differential signals to determine two unknowns). So the SCOL target includes in this case four cells, two for X-overlay and two for Y-overlay measurement.

There are several ways to obtain anti-symmetric differential signals. In one embodiment, cross-polarization signals are measured. In this case, two measurements are carried out on each cell. The first measurement is carried out with a first polarization (e.g., V-polarization) selected in the illumination path, and a second polarization (e.g., H-polarization) in the collection path, and the second measurement with the second polarization (e.g., H-polarization) in illumination and the first polarization (e.g., V-polarization) in collection. The first and second polarizations are orthogonal and mutually exclusive. The difference between the two signals obeys the anti-symmetry condition.

In another embodiment, anti-symmetric differential signals are obtained with an optical configuration that includes polarizers in combination with waveplates. The difference between signals measured with proper relative angles between the polarizers and waveplates obeys the anti-symmetry condition. An advantage of such a measurement scheme is that it allows flexibility in the polarization and phase content of the signal for optimal sensitivity to overlay. In addition, such an optical configuration can be tuned to have optimal overlay sensitivity for relatively small angles of incidence. In this case, illumination pupil apodization can be used to effectively reduce spot size without loss of sensitivity to overlay.

A third embodiment is specific to target designs in which both patterns are two-dimensional gratings. In this case, the two cells for X-overlay measurement have different programmed offsets in the X-direction and the same (but non-zero) offset in the Y-direction. The two measurements on each cell correspond to opposite illumination azimuth angles (e.g., 45 degrees and −45 degrees). The difference between such signals obeys the anti-symmetry condition. For this embodiment, it is advantageous to use an optical architecture with a detector in the pupil plane, since in this case the two signals from a given cell are collected simultaneously, in different pixels of the detector. In addition, many independent anti-symmetric signals can be collected simultaneously, corresponding to additional azimuth angles and angles of incidence.

A fourth embodiment also uses target designs in which both patterns are two-dimensional gratings. In this case, the target includes only three cells, all having programmed offsets in both the X and Y directions. The programmed offsets are such that the X-overlay measurement uses cells 1 and 2, while the Y-overlay measurement uses cells 2 and 3. Let us denote the programmed offset of cell i in the X and Y directions by $v_i^{(x)}$, and $v_i^{(y)}$, respectively. Examples of appropriate offsets are:

$$v_1^{(x)} = -v_2^{(x)} = -v_3^{(x)} = f_0^{(x)}; v_1^{(y)} = v_2^{(y)} = -v_3^{(y)} = f_0^{(y)}$$

$f_0^{(x)}$ and $f_0^{(y)}$ are offsets significantly smaller than the pattern pitches. For example, these offsets can be on the order of 10 nm or 15 nm. As in the third embodiment, anti-symmetric signals are collected from each cell as the difference between signals of opposite illumination azimuth angles.

Another embodiment relates to a scatterometry method. The method includes producing light having different polarizations, which may be performed as described further herein (e.g., using one or more light sources described further herein). The method also includes separating the light into two different light beams having orthogonal and mutually exclusive polarizations, which may be performed as described further herein (e.g., using a PBS described further herein). In addition, the method includes directing the two different light beams to a wafer, which may be performed as described further herein (e.g., using two or more first optical elements described further herein). The method further includes controlling which one of the two different light beams illuminates the wafer during measurements, which may be performed as described further herein (e.g., using one or more second optical elements configured as described herein). The method also includes separately detecting two different scattered light beams resulting from illuminating the wafer with the one of the two different light beams, which may be performed as described further herein (e.g., using a detection subsystem described herein). In addition, the method includes separately generating output responsive to the two different scattered light beams, which may be performed as described further herein (e.g., using a detection subsystem configured as described herein). The two different scattered light beams have orthogonal and mutually exclusive polarizations. All optical surfaces used for steps of the method are stationary during the measurements. The method further includes determining a characteristic of features formed on the wafer using the output, which may be performed as described further herein (e.g., using a computer subsystem configured as described herein).

The method may also include storing results of any of the step(s) of the method in a non-transitory computer-readable storage medium. The results may include any of the results described herein (e.g., a characteristic of features formed on the wafer) and may be stored in any manner known in the art. The storage medium may include any suitable storage medium known in the art. After the results have been stored, the results can be accessed in the storage medium and used as described herein, formatted for display to a user, used by another software module, method, or system, etc.

The method described above may include any other step(s) of any method(s) described herein. In addition, the method described above may be performed by any scatterometer embodiments described herein.

The embodiments described herein have a number of advantages over other systems and methods for scatterometry. For example, the illumination and collection polarizations states can be rapidly selected and changed using substantially high speed shutters. In addition, any permutation of illumination and collection polarization (e.g., H and V linear polarizations) can be selected. Furthermore, all optical components of the optical subsystem used for measurements are stationary. As such, there are no demands on the mechanical precision of the optical subsystem, scatterometer, or scatterometry method. In addition, there are no repeatability concerns. Furthermore, system calibrations are stable over time. Multiple PBS's on both illumination and collection paths generate a substantially high degree of polarization purity. Sharing of a PBS by illumination and collection paths also ensures perfect alignment between illumination and collection axes. Minimal components located between the "common" PBS and the wafer minimizes polarization disruption and polarization contamination. In addition, the light efficiency of the embodiments described herein is comparable to currently used methods and systems for scatterometry.

Further modifications and alternative embodiments of various aspects of the invention will be apparent to those skilled in the art in view of this description. For example, systems and methods for discrete polarization scatterometry are provided. Accordingly, this description is to be construed as illustrative only and is for the purpose of teaching those skilled in the art the general mariner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. An optical subsystem of a scatterometer, comprising:
   one or more light sources configured to produce light having different polarizations;
   a polarizing beam splitter configured to separate the light into two different light beams having orthogonal and mutually exclusive polarizations;
   two or more first optical elements configured to direct the two different light beams to a wafer;
   one or more second optical elements configured to control which one of the two different light beams illuminates the wafer during measurements; and
   a detection subsystem configured to separately detect two different scattered light beams resulting from illumination of the wafer with only the one of the two different light beams and to separately generate output responsive to the two different scattered light beams, wherein the two different scattered light beams have orthogonal and mutually exclusive polarizations, and wherein all optical surfaces of the optical subsystem used for the measurements are stationary during the measurements.

2. The optical subsystem of claim 1, wherein the two or more first optical elements comprise a first non-polarizing beam splitter and an additional polarizing beam splitter, both positioned in the path of a first of the two different light beams, and a second non-polarizing beam splitter and the additional polarizing beam splitter, both positioned in the path of a second of the two different light beams.

3. The optical subsystem of claim 2, further comprising an objective configured to direct tight from the additional polarizing beam splitter to the wafer and to collect light scattered from the wafer, wherein the light scattered from the wafer is separated into the two different scattered light beams by the additional polarizing beam splitter.

4. The optical subsystem of claim 3, further comprising a waveplate positioned between the objective and the additional polarizing beam splitter.

5. The optical subsystem of claim 2, wherein the detection subsystem comprises the first nm-polarizing beam splitter, the additional polarizing beam splitter, and the second non-polarizing beam splitter, wherein the additional polarizing beam splitter and the first non-polarizing beam splitter are positioned in a path of one of the two different scattered light beams, wherein the additional polarizing beam splitter and the second non-polarizing beam splitter are positioned in a path of another of the two different scattered light beams, and wherein the two different scattered light beams travel along optical paths along which the two different light beams used to illuminate the wafer travel.

6. The optical subsystem of claim 1, wherein the scatterometer is configured to control the one or more second optical elements such that the two different light beams illuminate the wafer sequentially.

7. The optical subsystem of claim 1, wherein the one or more second optical elements comprise a first shutter configured to be positioned in the path of a first of the two different light beams and a second shutter configured to be positioned in a path of a second of the two different light beams.

8. The optical subsystem of claim 1, wherein the detection subsystem is further configured to detect the two different scattered light beams sequentially.

9. The optical subsystem of claim 1, wherein the detection subsystem comprises a first shutter configured to be positioned in the path of a first of the two different scattered light beams and a second shutter configured to be positioned in the path of a second of the two different scattered light beams, and wherein the first and second shutters control which of the two different scattered light beams reaches a detector of the detection subsystem.

10. The optical subsystem of claim 1, wherein the detection subsystem is further configured to detect the two different scattered light beams simultaneously.

11. The optical subsystem of claim 1, wherein the detection subsystem is further configured to direct the two different scattered light beams to two different detectors simultaneously.

12. The optical subsystem of claim 1, wherein the one or more light sources comprise two or more lasers, each configured to generate a different wavelength of light, wherein a shutter and a dichroic combiner are coupled to each of the two or more lasers, and wherein light from the dichroic combiners is directed to a Pockels cell before being directed to the polarizing beam splitter.

13. The optical subsystem of claim 1, wherein the one or more light sources comprise two or more lasers, each configured to generate a different wavelength of light, wherein a dichroic combiner is coupled to each of the two or more lasers, and wherein light from the dichroic combiners is directed to an acousto-optical deflector before being directed to the polarizing beam splitter.

14. The optical subsystem of claim 13, further comprising a Pockels cell positioned between the dichroic combiners and the acousto-optical deflector.

15. The optical subsystem of claim 1, wherein the one or more light sources comprise two or more lasers, each configured to generate a different wavelength of light, wherein a dichroic combiner is coupled to each of the two or more lasers, wherein light from the dichroic combiners is directed to a Pockels cell before being directed to the polarizing beam splitter, and wherein the one or more second optical elements comprise two acousto-optical deflectors.

16. The optical subsystem of claim 1, further comprising a control subsystem configured to control one or more wavelengths of the light produced by the one or more light sources.

17. The optical subsystem of claim 16, wherein the measurements comprise critical dimension measurements.

18. The optical subsystem of claim 16, wherein the control subsystem is further configured to control the one or more wavelengths by stabilizing spectral output of the one or more light sources.

19. The optical subsystem of claim 16, wherein the control subsystem is further configured to control the one or more wavelengths by scanning the light produced by the one or more light sources over a restricted wavelength range.

20. The optical subsystem of claim 1, further comprising a pupil conjugate filter positioned in a pupil plane of the optical subsystem, wherein characteristics of the pupil conjugate filter vary as a function of location across the pupil conjugate filter.

21. The optical subsystem of claim 17, wherein the optical subsystem has illumination/collection symmetry.

22. The optical subsystem of claim 1, wherein the measurements comprise angle-resolved scatterometry measurements.

23. The optical subsystem of claim 1, wherein the measurements comprise multiple wavelength scatterometry measurements.

24. The optical subsystem of claim 1, wherein the measurements comprise spectroscopic scatterometry measurements.

25. The optical subsystem of claim 1, wherein a spot size of said only the one of the two different light beams that illuminates the wafer enables illumination of multiple cycles of a target structure on the wafer.

26. The optical subsystem of claim 25, wherein the illumination of the multiple cycles of the target structure allows diffraction orders of the two different scattered light beams collected in a pupil image of the detection subsystem to be localized and non-overlapping, and wherein the scatterometer comprises a computer subsystem configured to use information from angular location and shape of the collected diffraction orders in a modeling procedure to predict characteristics of the target structure.

27. The optical subsystem of claim 1, further comprising a multiple pole aperture positioned in an illumination pupil of the optical subsystem.

28. The optical subsystem of claim 1, wherein the measurements comprise measurements of differential-signal scatterometry overlay.

29. The optical subsystem of claim 28, wherein the measurements further comprise two signals measured from each cell of a target, and wherein a difference between the two signals is an anti-symmetric function of an offset between patterns in said each cell.

30. The optical subsystem of claim 29, wherein the two signals are cross-polarization signals.

31. The optical subsystem of claim 29, wherein the two or more first optical elements and the detection subsystem comprise polarizers in combination with waveplates, and wherein relative angles between the polarizers and the waveplates cause the difference between the two signals to obey an anti-symmetry condition.

32. The optical subsystem of claim 29, wherein the target comprises two-dimensional gratings in said each cell, and wherein the two signals measured from said each cell correspond to opposite illumination azimuth angles.

33. The optical subsystem of claim 32, wherein the detection subsystem comprises a detector in a pupil plane of the detection subsystem configured to collect the two signals from said each cell simultaneously in different pixels of the detector.

34. A scatterometer, comprising:
one or more light sources configured to produce light having different polarizations;
a polarizing beam splitter configured to separate the light into two different light beams having orthogonal and mutually exclusive polarizations;
two or more first optical elements configured to direct the two different light beams to a wafer;
one or more second optical elements configured to control which one of the two different light beams illuminates the wafer during measurements;
a detection subsystem configured to separately detect two different scattered light beams resulting from illumination of the wafer with only the one of the two different light beams and to separately generate output responsive to the two different scattered light beams, wherein the two different scattered light beams have orthogonal and mutually exclusive polarizations, and wherein all optical surfaces used for the measurements are stationary during the measurements; and
a computer subsystem configured to determine one or more characteristics of features formed on the wafer using the output.

35. A scatterometry method, comprising:

producing light having different polarizations;

separating the light into two different light beams having orthogonal and mutually exclusive polarizations;

directing the two different light beams to a wafer;

controlling which one of the two different light beams illuminates the wafer during measurements;

separately detecting two different scattered light beams resulting from illuminating the wafer with only the one of the two different light beams;

separately generating output responsive to the two different scattered light beams, wherein the two different scattered light beams have orthogonal and mutually exclusive polarizations, and wherein all optical surfaces used for steps of the method are stationary during the measurements; and determining a characteristic of features formed on the wafer using the output.

* * * * *